United States Patent [19]

Rahlwes

[11] Patent Number: 4,655,484
[45] Date of Patent: Apr. 7, 1987

[54] ISOMERIZATION PROCESS

[75] Inventor: William C. Rahlwes, Old Ocean, Tex.

[73] Assignee: Phillips Petroleum Company, Bartlesville, Okla.

[21] Appl. No.: 450,491

[22] Filed: Dec. 16, 1982

[51] Int. Cl.$^4$ .............................................. C07C 5/22
[52] U.S. Cl. .................................. 585/253; 585/350; 585/365; 585/371
[58] Field of Search ............... 585/251, 253, 350, 365, 585/371

[56] References Cited

U.S. PATENT DOCUMENTS

| | | | |
|---|---|---|---|
| 2,953,606 | 9/1960 | Dean et al. | 585/253 |
| 3,150,195 | 9/1964 | Findlay | 585/253 |
| 3,233,001 | 2/1966 | Merryfield et al. | 585/253 |
| 3,248,438 | 4/1966 | Kron | 585/253 |
| 3,249,642 | 5/1966 | Walaby et al. | 585/253 |
| 3,250,819 | 5/1966 | Caggage | 585/253 |
| 3,260,762 | 7/1966 | Cabbage | 585/253 |
| 3,264,361 | 8/1966 | Schellenberg | 585/253 |
| 3,311,667 | 3/1967 | Cabbage | 585/253 |

FOREIGN PATENT DOCUMENTS 606798  8/1948  United Kingdom ................ 585/365

Primary Examiner—William R. Dixon, Jr.
Assistant Examiner—Cynthia A. Prezlock
Attorney, Agent, or Firm—C. F. Steininger

[57] ABSTRACT

A hexanes stream, including normal hexane, isohexanes, methylcyclopentane and cyclohexane is isomerized by first fractionating the hexanes stream in a first fractionation step to produce a normal hexane-isohexanes rich overhead stream and a methylcyclopentane-cyclohexane rich bottoms stream, the bottom stream of the first fractionation step is isomerized to maximize the conversion of methylcyclopentane to cyclohexane, the overhead stream from the first fractionation step is fractionated in a second fractionation step to produce an isohexane rich overhead stream and a normal hexane rich bottoms stream, the effluent from the isomerization step is fractionated in at least one stage of a third fractionation step to produce a cyclohexane rich bottoms fraction and a methylcyclopentane-isohexane rich overhead stream and at least a part of the overhead stream from the third fractionation step is recycled to at least one of the isomerization steps and the first fractionation step. In one mode of operation, the overhead from the first stage of the third fractionation step is separated into an overhead stream rich in isohexanes which is combined with the overhead from the first fractionation step and passed to the second fractionation step and a bottoms stream rich is methylcyclopentane is thus recycled to the isomerization step or the first fractionation step. In a second mode of operation, the overhead from the first stage of the third fractionation step is recycled directly to the isomerization step and/or the first fractionation step.

6 Claims, 1 Drawing Figure

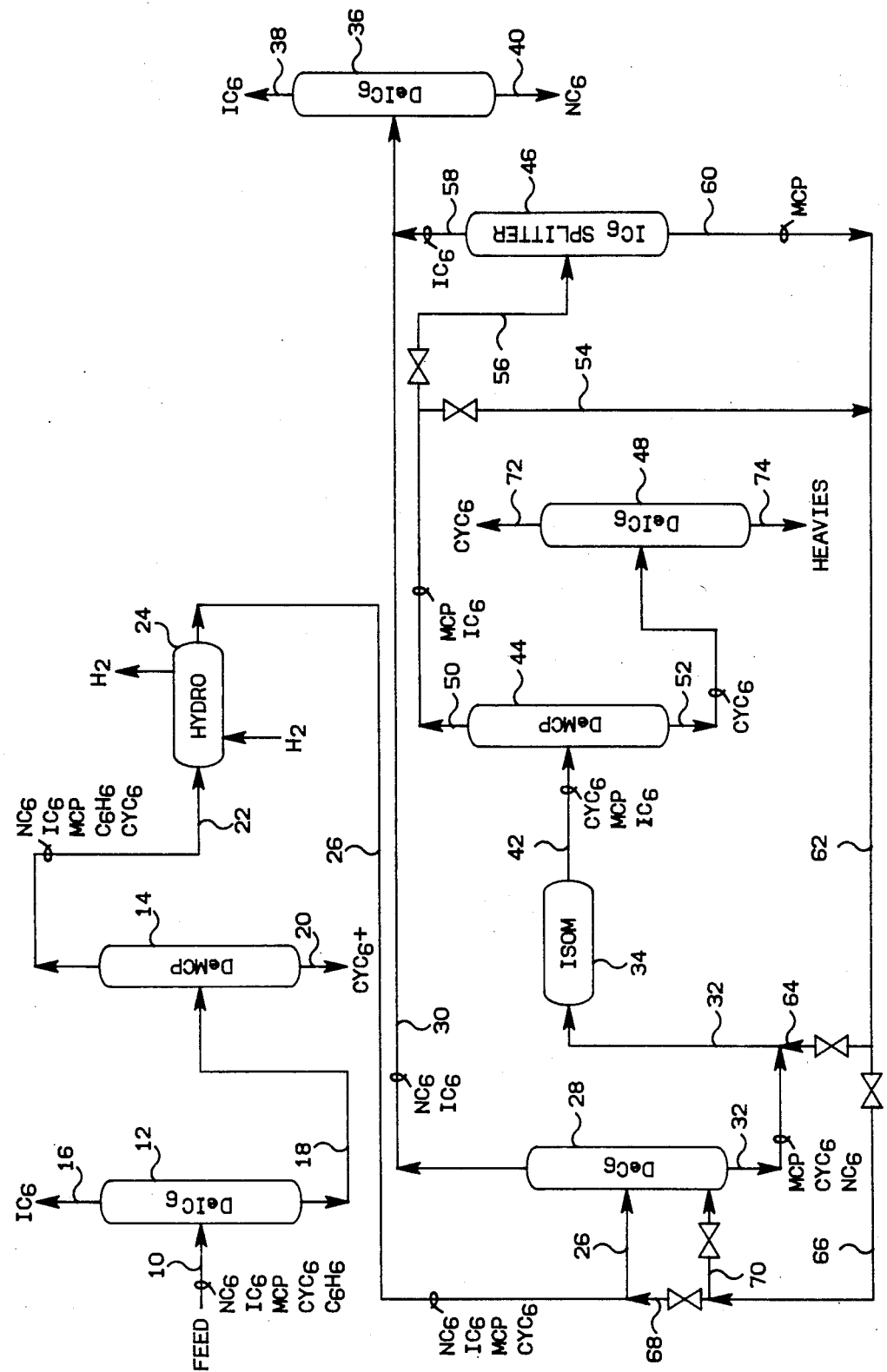

ISOMERIZATION PROCESS

The present invention relates to an improved process for the isomerization of $C_6$ hydrocarbons. More specifically, the present invention relates to an improved process for the isomerization of $C_6$ hydrocarbon streams to maximize the conversion to cyclohexane and the recovery of normal hexane.

BACKGROUND OF THE INVENTION

Refinery streams normally subjected to isomerization contain varying amounts of normal hexane, isohexanes, methylcyclopentane, cylcohexane and benzene. In the isomerization of such feedstreams, the feedstream is first treated with hydrogen to hydrogenate benzene to cyclohexane. Thereafter, the resulting product is isomerized, primarily to convert methylcyclopentane to cyclohexane. Consequently, one of the problems involved in such isomerization processes is maximizing cyclohexane production, since this material is a valuable chemical intermediary. During the course of such isomerization, normal hexane present in the feed to the isomerization is converted to isohexane. However, although isohexanes are useful as motor fuel blending stocks, the normal hexane, which is useful as a solvent, is substantially more valuable than isohexanes. Consequently, another problem involved is the recovery of normal hexane during the processing of the feedstream and, to the extent possible, suppressing the production of isohexanes from normal hexane. As in any other catalytic process, it is highly desirable to reduce the load or throughput to the isomerization step, since this will normally lengthen the life of the catalyst, improve conversion to desired products, and conserve energy. Since such isomerization systems include a large number of fractionation stages in order to separately recover normal hexane, isohexanes and cyclohexane, as products, such a system is highly energy intensive. Consequently, it is yet another problem to reduce the energy requirements of the system.

SUMMARY OF THE INVENTION

It is therefore an object of the present invention to provide an improved isomerization system which overcomes the above mentioned and other problems of the prior art. Another object of the present invention is to provide an improved isomerization system which maximizes the conversion of methylcyclopentane to cyclohexane. A further object of the present invention is to provide an improved isomerization system which maximizes the recovery of normal hexane from a $C_6$ hydrocarbon feedstream. Another and further object of the present invention is to provide an improved isomerization system which reduces fractionation for the recovery of products. A still further object of the present invention is to provide an isomerization system which reduces the energy requirements. Yet another object of the present invention is to provide an improved isomerization system which reduces the volume of feed to the isomerization step. A further object of the present invention is to provide an improved isomerization system which extends catalyst life and reduces losses from the isomerization step. These and other objects of the present invention will be apparent from the following description.

In accordance with the present invention, a hexanes stream, including normal hexane, isohexanes, methylcyclopentane and cyclohexane, is isomerized by fractionating the hexane stream in a first fractionation step to produce an overhead rich in normal hexane and isohexane and a bottoms stream rich in methylcyclopentane and cyclohexane. The bottoms stream is isomerized to convert methylcyclopentane to cyclohexane. The overhead stream from the first fractionation step is fractionated in a second fractionation step to produce an overhead stream rich in isohexanes and a bottoms stream rich in normal hexane, the effluent from the isomerization step is fractionated in a third fractionation step to produce a bottoms fraction rich in cyclohexane and an overhead stream rich in methylcyclopentane and isohexane and at least a part of the overhead stream from the third fractionation step is recycled to the isomerization step and/or the first fractionation step. In an alternative operation, all or a part of the overhead stream from the third fractionation step is further fractionated to produce an overhead stream rich in isohexanes and a bottoms stream rich in methylcyclopentane and the bottoms stream from the further fractionation is thus recycled to the isomerization step and/or the first fractionation step.

BRIEF DESCRIPTION OF THE DRAWING

The single figure of the drawings shows a flow diagram of an isomerization system in accordance with the present invention.

DESCRIPTION OF THE PREFERRED EMBODIMENTS

A typical refinery feedstream contains normal hexane, isohexanes, methylcyclopentane, cyclohexane and benzene. Such a feedstream is fed to the system through line 10 of the figure. In order to reduce the load on the hereinafter described hydrogenation unit and the herinafter described isomerization unit, it is generally desirable to preliminarily remove as much of the isohexanes and cyclohexane as possible prior to treatment. Accordingly, the feed from line 10 is passed through a preliminary fractionation step including a first stage 12 and a second stage 14. In first stage 12, an overhead stream rich in isohexanes is discharged through line 16 and a bottoms fraction, containing normal hexane, the remaining isohexanes, methylcyclopentane, cyclohexane and benzene, is discharged through line 18. The bottoms is then fed to the second stage 14 of the preliminary fractionation step, where it is separated into a bottoms fraction rich in cyclohexane which is discharged through line 20 and an overhead stream, containing normal hexane, isohexanes, methylcyclopentane, the remaining cyclohexane and benzene, is discharged through line 22. This overhead stream is then hydrogenated to convert the benzene to cyclohexane, by passage through hydrogenation step 24. Benzene hydrogenation step 24 can be any known hydrogenation type process for converting benzene to cyclohexane under conditions to maximize such conversion. Generally, the temperature in the hydrogenation zone will range from about 350° F. to about 450° F. at a pressure from about 400 psig to about 500 psig. Suitable catalysts that can be employed include conventional nickel catalysts and platinum catalysts. Any suitable type of contacting technique may be utilized such as a fixed bed, a moving bed, etc.

The effluent from the hydrogenation step 24 is passed through line 26. This feed comprises primarily normal hexane, isohexanes, methylcyclopentane, and cyclohexane. Conventionally, all of this stream is fed to the hereinafter mentioned isomerization step. In order to reduce the load on the hereinafter mentioned isomerization step, thus preventing buildup of isohexanes in the isomerization unit and the passage of normal hexanes through the isomerization unit and thus the reduction in a conversion of normal hexane to isohexanes. The hexanes stream from line 26 is fractionated in a first fractionation step 28. In fractionation step 28, an overhead stream rich in normal hexane and isohexanes is separated and discharged through line 30. The remainder of the feed, comprising primarily methylcyclopentane, cyclohexane and any remaining normal hexane, is discharged as a bottoms through line 32. As is pointed out hereinafter, this separation also slightly increases the recovery of normal hexane, which is the more valuable of normal hexane and isohexanes, eliminates at least one fractionation stage, hereinafter described, for the recovery of products and thus saves substantial amounts of energy. In any event, only the bottoms fraction from fractionation step 28 is fed to isomerization unit 34. It is estimated that the feed to isomerization unit 34 is therefor reduced to about one-third of that which would occur if all of the feed stream from line 26 were isomerized. This reduction in the feed has a number of advantages, including; reducing energy requirements, extending the contact time, increasing the conversion of methylcyclopentane to cyclohexane, and reducing catalyst losses, such as the loss of aluminum chloride and hydrogen chloride. As previously indicated, the recovery of normal hexane is increased and the production of isohexanes in isomerization unit 34 is reduced. The latter follows from the fact that about 30 to 70 percent of normal hexanes present in the feed to an isomerization unit is generally converted to isohexanes. The isomerization is carried out in a conventional manner in the presence of a suitable catalyst under conditions conducive to the optimization of the conversion of methylcyclopentane to cyclohexane. General reaction conditions include a temperature of about 150° F. to about 160° F. at a pressure of about 150 psig to about 170 psig. The residence time usually is in the range of about 30 minutes to about 90 minutes. A suitable conventional catalyst is used, for example, an aluminum chloride complex and any conventional contacting techniques such as a fixed bed, a moving bed or the like. Other catalysts that can be used include conventional platinum or alumina type catalysts. The overhead from the first fractionation step and passing through line 30 is then further fractionated in a second fractionation step 36, wherein the stream is separated into an isohexane rich stream discharged through line 38 and a normal hexane rich stream which is discharged through line 40. In conventional practice, this second fractionation step comprises two stages. Consequently, by operating in accordance with the present invention, one of the two stages, normally used, is eliminated and a single stage is employed in the second fractionation step. The obvious benefits of this are those previously pointed out and those which will be apparent to one skilled in the art. The effluent from the isomerization unit 34 is discharged through line 42 and includes primarily cyclohexane, unreacted methylcyclopentane and isohexanes. This effluent stream is then further fractionated in a third fractionation step, including; a first stage 44, a second stage 46 and a third stage 48. In first stage 44, an overhead stream rich in methlcyclopentane and isohexanes is separated and discharged through line 50 and a bottoms fraction rich in cyclohexanes and heavier is discharged through line 52. The overhead stream can be directly recycled through line 54 to the isomerization step 34 and/or to the fractionation step 28 and/or passed through line 56 to the second stage 46 of the third fractionation step. In the second stage 46, the overhead stream is further separated into an overhead stream rich in isohexanes, which is discharged through line 58, and a bottoms stream rich in unreacted methylcyclopentane, which is discharged through line 60 for recycle. As previously indicated, such recycle methylcyclopentane can be passed through line 62 and recycled to either isomerization step 34 or fractionation step 28 by passing the same through lines 64 or 66, respectively. As another alternative, recycle stream from line 66 can be passed through line 68 and combined with the feed to fractionation step 28 and/or, preferably, passed through line 70 adjacent the bottom of fractionator 28. In the latter instance, the heavy nature of the recycle stream permits this stream to be utilized as a stripping medium in fractionation zone 28.

In an alternative operation, the overhead from fractionation stage 44 is passed through line 54, then directly recycled to either isomerization step 34 or the first fractionation step 28, as previously described. Obiously, this latter mode of operation eliminates yet another stage of fractionation, namely the second stage 46 of the third fractionation step. This mode of operation has a number of advantages, including prevention of the buildup of isohexanes in the isomerization unit. This also recovers most of the methylcyclopentane with only a slight increase in energy requirements for the other fractionation stages and steps and it simplifies product control. Obviously, another stage of fractionation is eliminated, thus resulting in yet further decreases in the energy requirements.

In either of the above-mentioned modes of operation, the bottoms stream from the first stage 44 of the third fractionation step is fed to the third stage 48 of the third fractionation step wherein it is separated into a cyclohexane rich overhead product, discharged through line 72, and the bottoms fraction containing materials heavier than cyclohexane, which is discharged through line 74.

The following calculated examples are rpresentative of typical operations in accordance with the two modes of the present invention, as described above in connection with the figure. The tables show the volume flow in barrels/hour of the major hydrocarbon components through certain of the flow lines. The numbers at the heads of the columns refer to the numbers corresponding to the flow lines of the figure. Table I represents the mode of operation in which the overhead stream from fractionation stage 44 of the third fractionation step is passed to second stage 46 of the third fractionation step and Table II represents the mode of operation in which the overhead from fractionation stage 44 is passed through line 54 for direct recycle.

TABLE I

| Bbl/hr | 26 | 30 | 32 | 60 | 32 + 60 | 42 | 52 | 50 | 58 | 30 + 58 | 38 | 40 |
|---|---|---|---|---|---|---|---|---|---|---|---|---|
| IC$_6$ | 57.6 | 57.6 | — | — | — | 2.3 | — | 2.3 | 2.3 | 59.9 | 39.8 | 20.1 |
| NC$_6$ | 68.4 | 64.4 | 4.0 | .5 | 4.5 | 2.2 | — | 2.2 | 1.7 | 66.1 | 1.8 | 64.3 |

TABLE I-continued

| Bbl/hr | 26 | 30 | 32 | 60 | 32 + 60 | 42 | 52 | 50 | 58 | 30 + 58 | 38 | 40 |
|---|---|---|---|---|---|---|---|---|---|---|---|---|
| MCP | 42.2 | 8.5 | 33.7 | 9.0 | 42.7 | 12.8 | .2 | 12.6 | 3.6 | 12.1 | — | 12.1 |
| $CyC_6$ | 16.0 | — | 16.0 | .5 | 16.5 | 43.8 | 43.3 | .5 | — | — | — | — |
| HVY | — | — | — | — | — | 1.5 | 1.5 | — | — | — | — | — |
| Totals | 183.7 | 129.0 | 53.7 | 10.0 | 63.7 | 62.6 | 45.0 | 17.6 | 7.6 | 138.1 | 40.6 | 96.5 |

TABLE II

| Bbl/hr | 26 | 54 | 26 + 54 | 32 | 42 | 52 | 72 | 74 | 30 | 38 | 40 |
|---|---|---|---|---|---|---|---|---|---|---|---|
| Flow | 185 | 18.8 | 203.8 | 68.4 | 67.2 | 48.4 | 47.1 | 1.3 | 135.9 | 36.6 | 99.3 |
| $IC_6$ | 58.6 | 2.2 | 60.8 | — | 2.2 | — | — | — | 60.8 | 34.6 | 26.2 |
| $NC_6$ | 68.7 | 2.1 | 70.8 | 4.3 | 2.1 | — | — | — | 66.5 | 2.0 | 64.5 |
| MCP | 42.2 | 14.0 | 56.2 | 47.6 | 14.3 | .3 | .3 | — | 8.6 | — | 8.6 |
| $CyC_6$ | 16.0 | .5 | 16.5 | 16.5 | 47.6 | 47.1 | 46.3 | .8 | — | — | — |
| HVY | — | — | — | — | 1.0 | 1.0 | .5 | .5 | — | — | — |

While specific reactions, conditions, items of equipment, flow schemes, and the like have been referred to in the prior description, it is to be understood that these specific recitals are for purposes of illustration and to set forth the best modes in accordance with the present invention and are not to be considered limiting.

That which is claimed:

1. A method for isomerizing a hexanes stream comprising normal hexane, isohexanes, methylcyclopentane and cyclohexane comprising:
   (a) fractionating said hexanes stream in a first fractionation step in a manner and under conditions to produce a normal hexane-isohexane rich overhead stream and a methylcyclopentane-cyclohexane rich bottoms stream;
   (b) isomerizing said bottoms stream from said first fractionation step in at least one isomerization step in the presence of an isomerization catalyst and under conditions sufficient to maximize the conversion of methylcyclopentane to cyclohexane;
   (c) fractionating said overhead stream from said first fractionation step in a second fractionation step, in a manner and under conditions to produce an isohexanes rich overhead stream as a product and a normal hexane rich bottoms stream as a product;
   (d) fractionating the effluent from said isomerization step in a first stage of a third fractionation step in a manner and under conditions to produce a cyclohexane rich bottoms stream as a product and a methylcyclopentane-isohexane rich overhead stream;
   (e) fractionating said overhead stream from said third fractionation step in a second stage of said third fractionation step to produce an isohexane rich overhead stream and a methylcyclopentane rich bottoms stream;
   (f) recycling said bottoms stream from said second stage of said third fractionation step to said first fractionation step; and
   (g) passing said overhead stream from said second stage of said third fractionation step to said second fractionation step along with said overhead stream from said first fractionation step.

2. A method in accordance with claim 1 wherein the bottoms stream from the second stage of the third fractionation step, thus recycled to the first fractionation step, is introduced into said first fractionation step at a point below the point of introduction of the hexanes stream.

3. A method in accordance with claim 1 wherein the bottoms stream from the first stage of the third fractionation step is additionally fractionated in a third stage of the third fractionation step in a manner and under conditions to produce a cyclohexane rich overhead stream and a heavier bottoms stream.

4. A method in accordance with claim 1 wherein the hexanes stream is obtained from an original feed stream additionally containing benzene by hydrogenating said original feed stream in the presence of a hydrogenation catalyst and hydrogen and under conditions sufficient to convert said benzene to cyclohexane.

5. A method in accordance with claim 4 wherein the original feed stream is preliminarily fractionated in at least one stage of a preliminary fractionation step in a manner and under conditions to produce separate streams, comprising isohexanes, cyclohexane, and benzene-normal hexane-isohexanes-methylcyclopentane-cyclohexane and said benzene-normal hexane-isohexanes-methylcyclopentane-cyclohexane stream is thus hydrogenated.

6. A method in accordance with claim 5 wherein the preliminary fractionation step comprises a first stage and a second stage, the original feed stream is fractionated in said first stage of said preliminary fractionation step in a manner and under conditions to produce an isohexanes rich overhead stream and a heavier bottoms stream, said bottoms stream is fractionated in said second stage of said preliminary fractionation step in a manner and under conditions to produce a cyclohexane rich bottoms stream and a lighter overhead stream and said overhead stream from said second fractionation stage of said preliminary fractionation step is thus hydrogenated.

* * * * *